United States Patent
Maimon et al.

[11] Patent Number: 5,350,693
[45] Date of Patent: Sep. 27, 1994

[54] MULTICHAMBER SYRINGE DEVICE FOR FUSING CELLS

[75] Inventors: Jonathan Maimon, Rego Park; Bruce S. Schneider, Great Neck; Kenneth C. Gorray, Fresh Meadows; Michele Mauro, Bayside, all of N.Y.

[73] Assignee: Long Island Jewish Medical Center, New Hyde Park, N.Y.

[21] Appl. No.: 44,400

[22] Filed: Apr. 8, 1993

[51] Int. Cl.$^5$ .................... C12M 1/00; C12M 1/02
[52] U.S. Cl. ................... 435/287; 435/316; 935/85
[58] Field of Search ............ 435/70.2, 70.21, 172.2, 435/240.26, 240.27, 284–287, 289, 290, 316; 935/52, 85, 89, 93; 422/99, 100; 428/402; 73/863.31, 863.32; 222/420; 239/422, 423, 426; 604/183, 187, 191, 239

[56] References Cited

U.S. PATENT DOCUMENTS

| | | | |
|---|---|---|---|
| H1,099 | 9/1992 | Sayler | 222/420 |
| 1,515,388 | 11/1924 | Hopkins | 239/422 |
| 3,764,115 | 10/1973 | Buckingham et al. | 222/333 |
| 4,022,575 | 5/1977 | Hansen et al. | 436/52 |
| 4,029,470 | 6/1977 | Wilkins et al. | |
| 4,179,339 | 12/1979 | Sogi et al. | 435/292 |
| 4,441,532 | 4/1984 | Hrubesh | 222/420 |
| 4,578,167 | 3/1986 | Schoner | 935/93 |
| 4,665,034 | 5/1987 | Chandler | |
| 4,689,204 | 8/1987 | Buck et al. | |
| 4,908,187 | 3/1990 | Holmquist et al. | |

FOREIGN PATENT DOCUMENTS

| | | | |
|---|---|---|---|
| 3317415 | 11/1984 | Fed. Rep. of Germany | 935/93 |
| 0251877 | 12/1985 | Japan. | |
| 3240477 | 10/1991 | Japan. | |

OTHER PUBLICATIONS

Campbell *Monoclonal Antibody Technology* N.Y., Elsevier, 1986, pp. 126–134.
Kennett, "Fusion Protocols" in: Kennett et al. *Monoclonal Antibodies* (N.Y., Plenum Press, 1980), pp. 365–371.

*Primary Examiner*—William H. Beisner
*Attorney, Agent, or Firm*—Amster, Rothstein & Ebenstein

[57] ABSTRACT

An apparatus for fusing cells which includes a multichamber syringe having a first chamber containing a suspension of cells, a second chamber containing a suspension of cells, and a third chamber containing at least 40% by volume polyethylene glycol (PEG). The exit passageways of the chambers being braided such that the downstream ends thereof are beveled and face one another at the same level. The relative cross sections of the chambers being of a diameter such that a desired ratio of the suspensions and solution form in midair a mixture of 15% to 25% PEG by volume. The apparatus also includes a non-linear tube in fluid communication with the syringe for receiving the mixture therefrom and a device for causing a reciprocating passage of the mixture through the non-linear tube.

5 Claims, 2 Drawing Sheets

MULTICHAMBER SYRINGE DEVICE FOR FUSING CELLS

BACKGROUND OF THE INVENTION

The present invention relates to method and apparatus for fusing cells to produce a variety of cell hybrids, and more particularly to such method and apparatus for use in hybridoma production with a high fusion-and-survival efficiency.

The conventional procedure for producing monoclonal antibodies, i.e., hybridomas, involves several steps. One critical step consists of fusing centrifuge-pelleted myeloma cells with selected cells (e.g., spleen cells) taken from a donor (e.g., immunized mouse). The two cell populations (suspensions) are gradually mixed together and fused using polyethylene glycol (PEG) of molecular weight 1500 Daltons in dropwise fashion at 50% by volume concentration in buffered solution. This adding and mixing continues for about one minute, and is then terminated by adding tissue culture media to stop the PEG-induced toxicity to the cells. The cells are then spun down, the toxic medium (PEG) is removed, and fresh non-toxic medium is added. The cells are then resuspended, and the yield of fused cells is determined by examination under a microscope. The cells are then plated in ninety-six well plates, with the aim of achieving one fused cell per well. A discriminatory medium is applied to the well plates. In this medium the myeloma X spleen fused cell hybrids will thrive, while other cells will either die or not grow during a short period.

Using this standard methodology, generally only 2-3% of the initial cell population are rendered fused, and only a few of these hybrid cells will survive and yield a monoclonal culture. Thus the "fusion-and-survival" efficiency is generally less than 3% and can be as low as 0.001%.

Accordingly, it is an object of the present invention to provide a method and apparatus for fusing cells to produce a variety of cell hybrids.

Another object is to provide such a method and apparatus for hybridoma production.

A further object is to provide such a method and apparatus which has a fusion-and-survival efficiency of at least 40%.

SUMMARY OF THE INVENTION

It has now been found that the above and related objects of the present invention are obtained in a method of fusing cells by providing separate suspensions of first cells and second cells to be added thereto, and a polyethylene glycol (PEG) solution. Both suspensions and the PEG solution are initially mixed together to provide a mixture of at least 15% PEG by volume and then the mixture is further mixed for at least 7 minutes by reciprocating passage thereof through a non-linear tube. Alternately, both suspensions and the PEG solution are initially mixed together in mid-air to provide a mixture of no more than 25% PEG by volume and then the mixture is further mixed for no more than 15 minutes by reciprocating passage thereof through a non-linear tube. As a final alternative, both suspensions and the PEG solution are initially mixed together to provide a mixture of 15%-25% PEG by volume and then the mixture is further mixed for 7-15 minutes by reciprocating passage thereof through a non-linear tube, the method being characterized by an overall fusion-and-survival efficiency of at least 40%. Typically the first cells are myeloma cells and the second cells are spleen cells.

In a preferred embodiment, prior to initial mixing, the second cells may be shrunk by exposing the same to hypertonic media. Prior to initial mixing, the PEG solution is at least 40% PEG by volume. Each separate suspension is gently agitated—e.g., by a flexible magnetic stirrer capable of vertical motion within the suspension. Preferably both suspensions and the solution are initially mixed in mid-air by simultaneously ejecting them from three separate chambers of a multi-chamber syringe, the exit passageways from the chambers being braided together so that the beveled downstream ends thereof face one another. The non-linear tube is helical, of small inner diameter, and is disposed in a water bath maintained at about 37° C., thereby warming mixture in the non-linear tube. Both suspensions and the mixture are maintained at about 37° C.

The present invention further encompasses apparatus for fusing cells comprising a multichamber syringe having a first chamber containing a suspension of myeloma cells, a second chamber containing a suspension of the cells to be added thereto, and a third chamber containing a solution of polyethylene glycol (PEG) which is at least 40% by volume. The first, second and third chambers define respective exit passageways of needles braided together with the downstream ends thereof beveled and facing one another, the relative cross sections of the chambers being of sufficient dimensions to provide a desired ratio of the various ingredients thereof for forming in midair a mixture of 15%-25% PEG by volume. A substantially horizontally disposed non-linear tube is in fluid communication with the syringe for receiving the mixture therefrom. Means are provided for causing a reciprocating passage of the mixture through the non-linear tube.

In a preferred embodiment, each of the three chambers of the multichamber syringe defines means enabling the filling thereof with the suspension or solution and the removal of air therefrom prior to passage of the suspension or solution through the respective exit passageways. Reservoir means for receiving the mixture from the syringe are in fluid communication with the non-linear tube at one end. The reciprocating passage-causing means is a single-chamber syringe at the other end of the non-linear tube, repeated actuation and deactuation of the single-chamber syringe causing a reciprocating passage of the mixture through the non-linear tube and between the non-linear tube and the reservoir means.

BRIEF DESCRIPTION OF THE DRAWING

The above and related objects, features, and advantages of the present invention will be more fully understood by reference to the following detailed description of the presently preferred, albeit illustrative, embodiments of the present invention when taken in conjunction with the accompanying drawing wherein.

DETAILED DESCRIPTION OF THE PREFERRED EMBODIMENTS

The present invention will be described hereinbelow in terms of method and apparatus for producing monoclonal antibodies (i.e., hybridomas) and in particular hybridomas formed by the fusion of myeloma cells and spleen cells. It will be appreciated, however, that the present invention may be used for fusing any cells and for the preparation of a variety of cell hybrids. The present invention provides a fusion-and-survival efficiency of at least 40% (that is, at least 40% of the cells used will fuse and survive to render a monoclonal culture) as opposed to the conventional methods which provide only 2-3% fusion with only a few of those hybrids surviving to render a monoclonal culture. Accordingly, the present invention permits a minimal number of cells to be used for fusion since the toxicity to the cells is very low and the survivability of the hybrids produced thereby is therefore extremely high.

Figure 1:
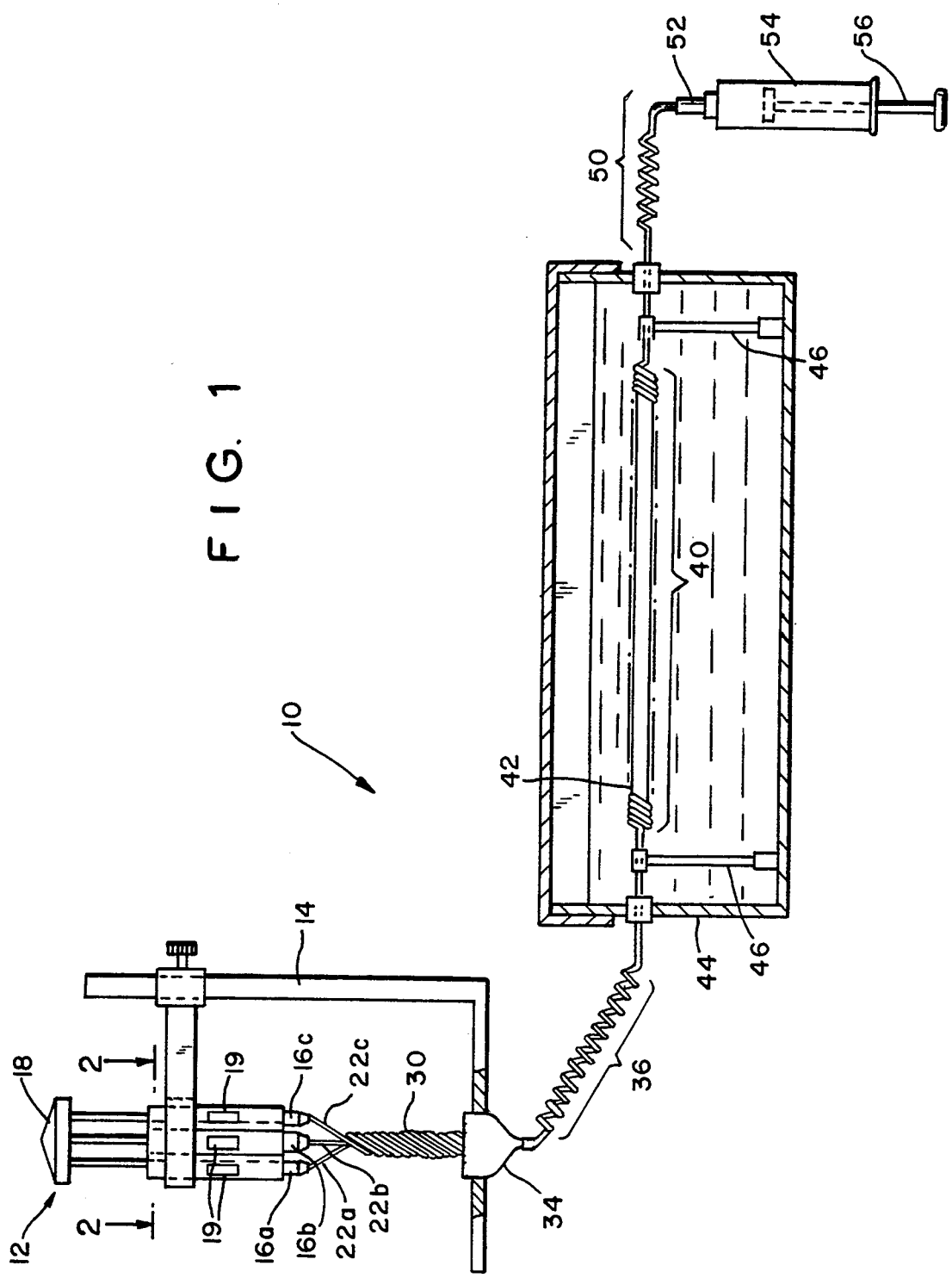
FIG. 1 is a schematic side elevational view, partially in section, of apparatus according to the present invention.

Referring now to the drawing, and in particular to FIG. 1 thereof, therein illustrated is apparatus according to the present invention, generally designated by the reference numeral 10. The apparatus 10 includes a multibarrel syringe generally designated by the reference numeral 12, conventionally supported on a syringe stand 14. The multibarrel syringe 12 has a plurality of barrels or chambers, three barrels 16a, 16b, 16c being illustrated. The three barrels 16a-16c are fitted with a common multishaft plunger 18, each shaft being at least partially disposed within a respective barrel. The common plunger head 18 enables each of the three shafts to be advanced within its respective barrel at the same speed so that the contents thereof may be ejected from the barrels 16a-16c at a constant volumetric rate, assuming that the bores or inner diameters of the barrels 16a-16c are identical.

Figure 2:
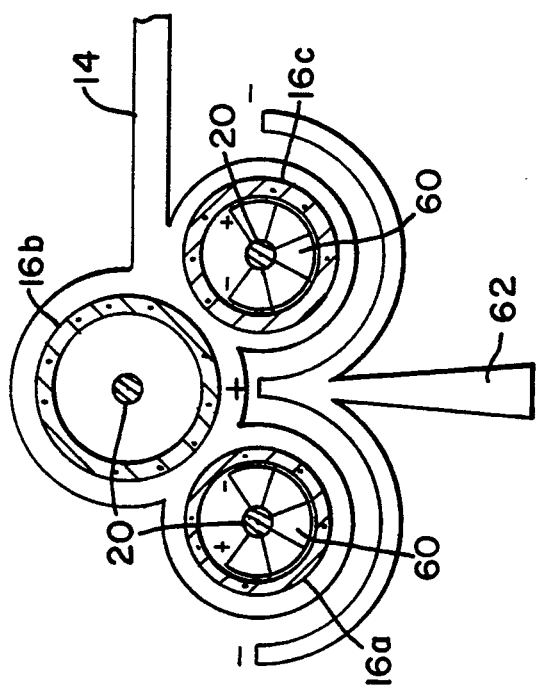
FIG. 2 is a sectional view taken along the line 2—2 of FIG. 1.

In point of fact, as best seen in FIG. 2, the size of the barrels 16a-16c (that is, their cross sectional areas) will vary from one to the other, depending upon the number of cells to be fused. The barrel 16b which will contain the polyethylene glycol (PEG) solution may have a 3 ml capacity and will be of greater bore size than either the barrel 16a used for the myeloma cells or the barrel 16c used for the spleen or other cells to be fused with the myeloma cells, each barrel 16a, 16c preferably having a 2 ml capacity. Preferably the PEG barrel 16b will have a bore with a cross sectional area twice that used for the cell barrels 16a, 16c. This permits a volume of PEG to be dispensed from barrel 16b which is greater than the volume of cells dispensed from each barrel 16a, 16c, while at the same time permitting the plunger 18 to end up at the same height for all three barrels, thus enabling application of a unified, level pressure to the multishaft common plunger 18. As will be appreciated by those skilled in the art, other means may be used to ensure the dispensing of smooth streams of three different components, with the streams being of predetermined relative volumetric flow rates.

In order to enable easy and rapid filling of the barrels 16a-16c of the syringe 12 under sterile conditions and without damage to the cell suspensions, each barrel preferably has at least one slit 19, and optimally two opposing slits 19, cut out of its sidewall. Each slit 19 is typically approximately 1.5-2 mm wide and 12-15 mm long, ending above the pre-fixed volume to be occupied by the contents of each barrel. Through one of the slits 19, a pre-fixed volume of the intended contents of the barrel (that is, either the myeloma cells, the spleen cells, or the PEG solution) will be applied to each barrel by pipette or the like. Thereafter, the plunger 18 will be depressed to almost the entirety of the slit length to express air from the barrel and thereby prevent evaporation of the media in which the cells are suspended and drying of the cells under biological safety cabinet (e.g., sterile hood) conditions. The plunger will be depressed further downward when fusion is started. The air that is forced out of the barrels 16a-16c by the shafts 20 of the plunger 18 will escape through the slits 19 prior to the time that the contents of any barrel is driven out of the syringe 12, thereby to reduce exposure of the cells to air. (If the barrels 16a-16c of the syringe 12 are so small (e.g., less than 0.5 ml) as to render the slits 19 unable to accommodate cell applications by pipette, then 2 mm diameter opposing holes (not shown) may be cut in each barrel as a substitute for the slits 19.)

Referring now to FIG. 2 in particular, in order to avoid precipitation of the cells within the syringe barrels 16a, 16c, a magnetic stirrer 60 may be placed in the bottom of each such barrel 16a, 16c. Before and during the fusion operation, this stirrer 60 can be lifted in an up-and-down or reciprocating vertical motion (i.e., above and below the plane of FIG. 2) by an external magnetic driver 62 shaped like the figure "3" that has been fitted to move freely between the barrels and vertically drive both stirrers 60 simultaneously, without rotating the same, so that they gently mix the contents of the barrels. One up-and-down stroke is typically sufficient to disperse the cells and prevent aggregation thereof. Each stirrer 60 is a hair-like plastic-coated magnetic wire shaped like a crescent with spokes. It is sufficiently soft that it does not prevent the shafts 20 from being fully inserted within the barrels 16a, 16c and reaching their full depth capacity.

A needle is secured to the bottom of each barrel, a smaller gauge needle 22a, 22c (e.g., a 28 gauge needle) being secured to the smaller gauge cell barrels 16a, 16c, respectively, and a larger gauge needle 22b (e.g., a 25 gauge needle) being secured to the larger gauge PEG barrel 16b. The greater diameter (i.e., lower gauge) of the PEG needle 22b enables a greater volume of PEG to be delivered relative to the volume of each of the cells delivered from the smaller diameter (i.e., higher gauge) needles 22a, 22c, preferably about twice the volume.

Figure 3:
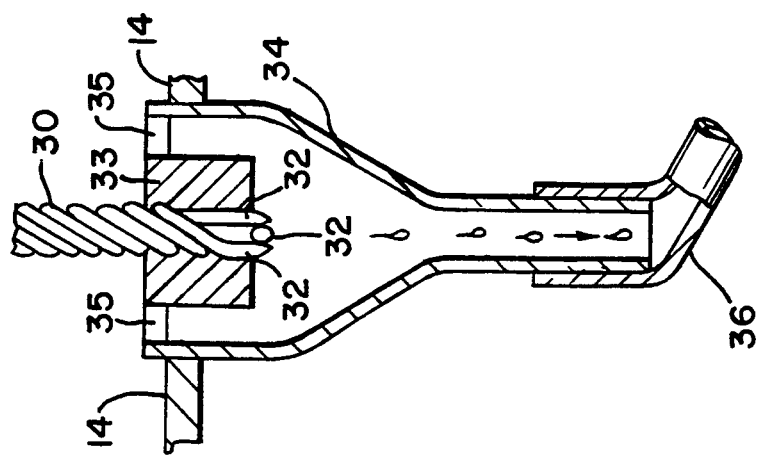
FIG. 3 is an enlarged view of the needle/cup interface.

It is a critical feature of the present invention that all three needles 22a-22c are united by a continuous twist or braiding 30 so that their beveled tips 32 will end up at the same level (i.e., height), with their bevels facing each other, as best seen in FIG. 3. The purpose of this is to enable the three droplets (from the three needle tips 32) to mix initially in mid-air as they fall into a small (e.g., 1.0 ml) cup or droplet receptacle 34 disposed about and below the beveled tips 32. Preferably the needles 22a-22c are braided to form cooperatively an external thread while the cup 34 includes a hollow central post 33 defining an internal thread and supported by spokes 35, the internal and external threads being adapted to be screwed together to maintain the needle braid 30 within the cup 34 as illustrated in FIG. 3. Of course, if desired, other mechanical arrangements may be used to secure and stabilize the needle braid 30 within cup 34.

The bottom of cup 34 communicates with an extended, loosely coiled tubing 36. The tubing 36 is tissue-culture compatible, with preferably a narrow 100-200 micron I.D. and a 1 mm O.D. The tubing 36 is firmly secured to the cup 34 so as to withstand the pressures achieved during operation of the method and extends downwardly from the bottom of cup 34 (preferably about six inches) before it becomes a helical coil 40.

The helical coil 40 may be formed by closely winding the tubing 36 onto a plastic rod 42 (preferably 12.5 cm long and 15 mm O.D.), thereby to create tightly adjacent loops or rings. Preferably the coil 40 includes about eighty rings or loops. The entire coil 40 is immersed in an insulated plastic box 44 (e.g., 15×5×5 cm) adapted to serve as a 37° C. water bath in a biological safety cabinet (i.e., a sterile tissue culture hood) for the fusion duration. The ends of coil 40 are secured to the box 44—e.g., by Y-shaped hooks 46 disposed at each end of rod 42 thereof and extending upwardly from the box bottom to the coil end.

Figure 4:
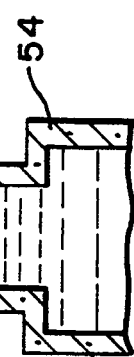
FIG. 4 is an enlarged view of the tubing/needle interface.

The coil 40 becomes an extended, uncoiled or loosely coiled tubing 50 (preferably about 12 cm long and an extension of tubing 36), that is in turn attached by a needle 52 (preferably 21 gauge) to a single barrel syringe 54 (preferably 10 ml) having a plunger 56, as best seen in FIG. 4. The single barrel syringe 54 serves as a receptacle for the fused cells as well as a fusion enhancer and is typically filled with 1.0 ml of a suspending medium. It enhances fusion by enabling the application of reciprocating (back and forth) pressure to the tubing 50, coil 40 and tubing 36 up to the cup or droplet receptacle 34 and back.

Once all the materials (cell suspension and PEG solution) have been ejected from the syringe 12, several back-and-forth strokes of the plunger 56 of the single barrel syringe 54 furthers the fusion by forcing materials to pass through the narrow gauge of the helical coil 40. Finally, the entire volume of materials is withdrawn into the single barrel syringe 54, and the syringe 54 is disconnected from the tubing 50. At this point, the contents of the syringe 54 are transferred to a tube with additional suspending media and spun down to collect the cells and dispose of the toxic supernatant.

The tubing 36, 50 at either end of the coil 40 need not be of any particular length and its purpose is to enable the easy and comfortable handling of the apparatus about the water box 44. Thus the tubing 36, 50 may be uncoiled or at least uncoiled relative to the tight coil 40. The total length of tubing 36, 40, 50 is generally about 100 cm. although it may be longer or shorter.

The inner diameter of the helical coil 40 (and hence the tubings 36, 50) must be carefully selected. Generally an inner diameter of 100 to 200 microns is preferred. If the inner diameter is too large, too many of the cells will be able to pass one another in the tubing without actually coming into contact with each other, thereby reducing the likelihood of fusion. On the other hand, if the inner diameter is too small, then the cells attempting to pass one another may clog the tubing, with resultant bursting of the tubing when pressure is applied thereto by syringe 54. The optimum diameter for the tubing of coil 40 is easily ascertainable by routine experimentation for any particular cell combination.

While the non-linear tubing 40 within the water bath box 44 has been shown and described in its preferred embodiment as a helical coil, the tubing 40 within the box 44 may alternatively have different non-linear configurations. A non-linear configuration is necessary so that there is some resistance within the tubing to flow of the cells therethrough, this resistance encouraging the mixing together of the cells and thereby promoting fusion. The helical coil configuration is preferred because it provides smoothly varying and uninterrupted resistance to passage of the cells under the influence of the pressure applied by syringe 54 and gravity. Other non-linear configurations for the tubing 40 within the box 44, such as zig-zag's, are also useful but are not as satisfactory—e.g., since the relatively sharp corners of a zig-zag tend to catch and hold the cells within corner pockets where they are not available for fusion.

The initial concentration of the PEG solution is at least 40% by volume and preferably the conventional 50% by volume. The mixture or droplet formed in mid-air from the three beveled needle ends is preferably 25% PEG by volume but may be as low as 15% PEG by volume. When the PEG is finally mixed with the cells to form the mixture which enters syringe 54, the PEG concentration is further reduced to preferably 15–20% by volume due to the suspending medium originally disposed in the single chamber syringe 54. As a result of the lower PEG concentration in the mixture with the cells, the fusion time may be extended from the conventional 1 minute to as much as 15 minutes with negligible damage being done to the cell suspensions. Preferably the PEG concentration is 15–20% by volume in the mixture within the helical coil 40 and the time of mixing is 7–15 minutes, with lower concentrations of PEG requiring longer mixing time and vice versa. Instead of spinning and pelleting the myeloma cells, cell suspensions of both the myeloma cells and the cells to be fused therewith (e.g., the spleen cells) can be used. This is believed to increase the probability of a fusion among the individual cells, thus contributing to the high fusion-and-survival efficiency of the present invention.

The method preferably includes shrinking of the spleen cells by hypertonic media containing a vital stain or dye before they are introduced into syringe 12. This results in deformation of the cell membrane, thereby forming multiple protrusions thereon and rendering more probable multiple cell-to-cell contacts with the myeloma cells suspended in isotonic media. This in turn increases the chances for fusion of the spleen and myeloma cells, again contributing to the high overall fusion-and-survival efficiency of the present invention. More particularly, the cells are disposed in a hypertonic media with 0.3M NaCl and the dye for five minutes prior to fusion. The dyed spleen cells are washed with media containing 0.3 NaCl to remove the excess dye and then resuspended in the same media to obtain the correct number of cells per volume for the fusion. The dye serves as a marker under the microscope to determine fusion efficiency by detecting spleen cells inside myeloma cells.

To utilize the apparatus illustrated in FIG. 1, the barrels 16a–16c of the multi-chamber syringe 12 are filled via the slits with the desired contents: 50% by volume buffered PEG at 37° C. for barrel 16b, a 37° C. myeloma cell suspension for barrel 16a, and a 37° C. spleen cell suspension for barrel 16c. The needles 22a–22c are secured to the appropriate barrels, and the needle braid 30 is secured to the post 33 of cup 34. The upstream end of coil 40 (i.e., the tubing 36) is secured to the bottom of cup 34, and the downstream end of coil 40 (i.e., the tubing 50) is secured via the needle 52 to syringe 54. The coil 40 is disposed within the 37° C. waterbath by securing the hooks 46 to either end of the rod 42. The single chamber syringe 54 is provided with about 1.0 ml of suspending medium.

To eject all air from the coil 40, the handle 56 of syringe 54 is moved upwardly into the barrel in order to fill the coil 40 (and tubings 36 and 50), all the way up to the cup 34, with the suspending medium originally present in the syringe 54.

As a further preliminary matter, if desired, the spleen cells may be shrunk by hypertonic media, as described above.

To begin the fusion process, a slow and continuous pressure is applied downwardly on the common multi-shaft plunger 18 of syringe 12 to cause about one drop at a time to fall into the cup 34. At the same time, the plunger 56 of the single barrel syringe 54 is withdrawn therefrom in order to allow the volume dropping from the cup 34 to enter the coil 40. After every few drops (preferably 2-3 drops) falling into cup 34, the plunger 56 is reciprocated within the syringe 54 a few times (about twice) in order to move the cells back and forth (in, along and out of coil 40) several times. Periodically, if necessary, the magnetic stirrers are cycled once in the barrels 16a, 16c to maintain the cell suspensions. This continues until the contents of all volumes of all three barrels 16a-16c of syringe 12 are used up. At this point the fused cells are moved in and out of coil 40 several more times (by reciprocating the handle 56 of syringe 54), and finally the plunger 56 is withdrawn to collect all of the cells within the barrel of syringe 54.

The syringe 54 is now disconnected from the system, and the cells are then transferred into another tube having fresh media. The new tube is then centrifuged, the toxic supernatant discarded, and the remaining pellet resuspended in fresh media. Ultimately, the cells are used to fill ninety-six well plates with approximately one fused cell per well. By using the method and apparatus of the present invention as described hereinabove, fusion-and-survival yields of at least 40%, and generally 40-80%, were obtained for the fusion of NS-1 myeloma cells with rat spleen cells, 50-100 fold greater than afforded by existing systems. The viable cells produced IgG which reacted with goat anti-rat IgG but not goat anti-rat IgM. The fused cells are grown at a rapid rate in selective media providing discriminatory nutrition.

To summarize, the present invention provides method and apparatus for fusing cells for production of a variety of cell hybrids, including hybridomas, with a fusion-and-survival efficiency of at least 40%, a 50-100 fold improvement over the known systems.

Now that the preferred embodiments of the present invention have been shown and described in detail, various modifications and improvements thereon will become readily apparent to those skilled in the art. Accordingly, the spirit and scope of the present invention is to be construed broadly and limited only by the appended claims, and not by the foregoing specification.

We claim:

1. Apparatus for fusing cells comprising:
   (A) a multichamber syringe having a first chamber containing a suspension of cells of a first type, a second chamber containing a suspension of cells of a second type to be added to the suspension of cells of a first type, and a third chamber containing at least 40% by volume polyethylene glycol (PEG) solution, said first, second and third chambers defining respective exit passageways braided together with the downstream ends thereof beveled and facing one another at the same level, the relative cross sections of said chambers being of sufficient dimensions to provide a desired ratio of the suspensions and solution for forming in midair a mixture of 15%-25% PEG by volume;
   (B) a substantially horizontally disposed non-linear tube in fluid communication with said syringe for receiving the mixture therefrom; and
   (C) means for causing a reciprocating passage of the mixture through said non-linear tube.

2. The apparatus of claim 1 additionally including reservoir means for receiving the mixture from said syringe, said non-linear tube being in fluid communication with said reservoir means at one end.

3. The apparatus of claim 2 wherein said means for causing is a single-chamber syringe at the other end of said non-linear tube, repeated actuation and de-actuation of said single-chamber syringe causing a reciprocating passage of the mixture through said non-linear tube and between said non-linear tube and said reservoir means.

4. The apparatus of claim 1 wherein each of said chambers defines a side wall and means in the form of at least one aperture in the chamber sidewall for enabling the filling thereof with the suspension or solution and for the removal of air therefrom, both prior to passage of said suspension or solution through said respective exit passageways.

5. The apparatus of claim 1 additionally including a flexible magnetic stirrer disposed in each of said first and second chambers and configured and dimensioned for vertical motion therein, and a magnetic driver for said stirrers disposed adjacent said first and second chambers for simultaneous vertical motion relative to said first and second chambers, thereby to cause said stirrers to gently agitate said suspensions.

* * * * *